(12) United States Patent
Zacharias et al.

(10) Patent No.: US 6,620,143 B1
(45) Date of Patent: *Sep. 16, 2003

(54) SANITARY NAPKIN ARTICLE HAVING BODY-FACING ADHESIVE

(75) Inventors: Duane Kenneth Zacharias, Appleton, WI (US); Yung Hsiang Huang, Appleton, WI (US); Frank Gerald Druecke, Oshkosh, WI (US)

(73) Assignee: Kimberly-Clark Worldwide, Inc., Neenah, WI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/935,348

(22) Filed: Sep. 22, 1997

Related U.S. Application Data

(63) Continuation-in-part of application No. 08/659,858, filed on Jun. 7, 1996, now Pat. No. 6,213,993, which is a continuation of application No. 08/331,072, filed on Oct. 28, 1994, now abandoned.

(51) Int. Cl.⁷ .......................... A61F 13/15; A61F 13/20
(52) U.S. Cl. .................... 604/385.03; 604/387
(58) Field of Search .................. 604/365, 366, 604/386, 387, 389, 390, 385.03

(56) References Cited

U.S. PATENT DOCUMENTS

| | | |
|---|---|---|
| 3,438,371 A | 4/1969 | Fischer et al. |
| 4,455,146 A | 6/1984 | Noda et al. .................. 604/897 |
| 4,460,364 A | 7/1984 | Chen et al. .................. 604/387 |
| 4,753,648 A | 6/1988 | Jackson ....................... 604/389 |

(List continued on next page.)

FOREIGN PATENT DOCUMENTS

| | | |
|---|---|---|
| DE | 3535574 | 4/1987 |
| GB | 2 284 767 | * 6/1995 |
| JP | 69622 | 2/1994 |
| WO | 8900106 | 1/1989 |

(List continued on next page.)

OTHER PUBLICATIONS

Kenny, J. F. et al., "Medical–Grade Acrylic Adhesives for Skin Contact," Journal of Applied Polymer Science, vol. 45, 355–361 (1992).

*Primary Examiner*—Karin Reichle
(74) *Attorney, Agent, or Firm*—Thomas J. Connelly; Paul Y. Lee; Douglas G. Glantz

(57) ABSTRACT

A sanitary napkin having a body-side adhesive is disclosed having an absorbent core with at least one body-facing surface designed to be positioned against the wearer's body and a pressure sensitive adhesive secured to the body-facing surface. In one aspect, the article is limited in dimension and includes a hot melt adhesive to be pressed against the wearer's pudendal region and characterized by a midblock Tg of less than $-10°$ C., a G' (storage modulus) less than $15 \times 10^4$ dynes/cm² at 10 rad/s. (25° C.), a G" (loss modulus) of 1 to $6 \times 10^4$ dynes/cm², a tensile strength greater than 10 psi, and requiring no subsequent curing operation after cooling. In one aspect, the article includes the adhesive to be pressed against the wearer's pudendal region has an adhesive weight less than 1500 mg per square inch and a tan delta residing inside a quadrangle ABCD wherein said quadrangle ABCD is defined by graphically plotting frequency in radians per second versus tan delta referenced to about 20° Centigrade of the adhesive, the quadrangle ABCD having as points A and D a tan delta of about 0.01 and about 0.6 respectively at a frequency of about 0.1 radians per second and points B and C at a tan delta of about 0.1 and about 1.7 respectively at a frequency of about 1000 radians per second.

7 Claims, 2 Drawing Sheets

U.S. PATENT DOCUMENTS

| | | | |
|---|---|---|---|
| 4,762,888 A | 8/1988 | Sun et al. ................ 525/125 |
| 4,784,653 A | 11/1988 | Bolton et al. ............. 604/307 |
| 5,114,419 A | 5/1992 | Daniel et al. ........... 604/385.1 |
| 5,559,165 A | 9/1996 | Paul ........................ 523/111 |
| 5,618,281 A * | 4/1997 | Betrabet et al. ........... 604/387 |
| 5,618,282 A * | 4/1997 | Schlangen ................. 604/387 |
| 5,658,270 A | 8/1997 | Lichstein .................. 604/387 |
| 5,807,367 A * | 9/1998 | Dilnik et al. .............. 604/387 |

FOREIGN PATENT DOCUMENTS

| | | | |
|---|---|---|---|
| WO | 9516424 | | 6/1995 |
| WO | 96/13238 | * | 5/1996 |
| WO | 9827909 | | 7/1998 |
| WO | 9827910 | | 7/1998 |
| WO | 9827911 | | 7/1998 |
| WO | 9827912 | | 7/1998 |
| WO | 9827913 | | 7/1998 |
| WO | 9827914 | | 7/1998 |
| WO | 9827915 | | 7/1998 |
| WO | 9827916 | | 7/1998 |
| WO | 9827917 | | 7/1998 |
| WO | 9827918 | | 7/1998 |
| WO | 9828014 | | 7/1998 |
| WO | 9828015 | | 7/1998 |
| WO | 9828016 | | 7/1998 |
| WO | 9828017 | | 7/1998 |
| WO | 9828018 | | 7/1998 |
| WO | 9828019 | | 7/1998 |
| WO | 9828020 | | 7/1998 |
| WO | 9828021 | | 7/1998 |
| WO | 9828022 | | 7/1998 |
| WO | 9828023 | | 7/1998 |
| WO | 9828024 | | 7/1998 |

* cited by examiner

SANITARY NAPKIN ARTICLE HAVING BODY-FACING ADHESIVE

This application is a continuation-in-part of prior U.S. patent application U.S. Ser. No. 08/659,858 filed Jun. 7, 1996, now U.S. Pat. No. 6,213,993, which is a continuation of U.S. patent application U.S. Ser. No. 08/331,072 filed Oct. 28, 1994, now abandoned.

BACKGROUND OF THE INVENTION

1. Technical Field

The present invention relates to a disposable absorbent article having a body-facing adhesive to be positioned against a wearer's skin. In one aspect, the invention relates to a catamenial device having a supportive adhesive residing on the body-side surface of the device.

2. Background

Externally positioned, disposable absorbent articles in the form of a catamenial device, configured for the absorption of body fluids such as menses, collectively are referred to herein as a sanitary napkin.

The sanitary napkin is secured during use, often by attaching the sanitary napkin to the wearer's undergarment by an adhesive.

INTRODUCTION TO THE INVENTION

When a sanitary napkin is secured to an undergarment, the wearer may experience a number of drawbacks or disadvantages. One drawback is that the adhesive can stick too aggressively to the inside surface of the undergarment leaving a residue. Another disadvantage is the napkin will tend to move with the undergarment rather than associating with the bodily movements of the wearer. This undesirable movement can result in a less secure fit and can increase the incidence of fluid leakage, irritation, chafing, and discomfort.

Attempts made to adhere a sanitary napkin directly to the wearer require an adhesive compatible with the wearer's skin. In securing the sanitary napkin directly to the wearer, adhesives of the type used in various surgical applications could be employed. However, removal of these adhesives causes sudden pain and discomfort to the wearer in the sensitive pudendal region.

Thus, sanitary napkins could be employed large enough to avoid applying such adhesive in contact with the wearer's pubic hair and sensitive genitalia. However, such large sanitary napkins are found to be uncomfortable to the wearer, and they are noticeable through the wearer's outer garments.

A sanitary napkin is needed which would be secured directly to the wearer's body, which would be comfortable to wear, which would be discrete in appearance as viewed through the wearer's outer garments, which would give the wearer a feeling of security during use, which would not cause discomfort upon removal from the wearer's skin and hair, and which would not cause discomfort upon removal from the wearer's skin and hair in the sensitive pudendal region.

Very few adhesive compositions are completely satisfactory for application to human skin. The requirements for such adhesives are stringent. They must adhere well to human skin during perspiration, when the weather is hot, or in an environment of draining wounds, yet be removable without leaving adhesive residue on the skin's surface. Adhesion should take effect immediately on application to skin, even in a hot or moist environment, and should release cleanly and with minimal discomfort when voluntarily removed in this environment.

Adhesives applied to sensitive areas of the human body require further special characteristics. Hair covered regions are especially difficult to adhere to well without causing pain upon removal of the adhered article. For such regions, a soft adhesive with specific viscoelastic properties is required. Hydrogels could be used effectively for such purposes, but hydrogels have their own disadvantages, including high price, special packaging and release layers to retain the moisture (typically about 40% of the total adhesive), as well as variations in properties during use in response to changes in humidity. Other disadvantages arise from the general necessity of a non-woven support to strengthen the adhesive and hold it in place during cure. When cured, a water impervious release layer is applied.

To obtain a soft adhesive while maintaining solid-like behavior requires high molecular weight polymers. With hydrogels, this is obtained by cross linking or curing after cooling, as is the case with an electron beam curable acrylic described in European Patent Application EP 175562 A2. Further, U.S. Pat. No. 5,262,468 to Chen describes the use of very high molecular weight rubbers to obtain gelatinous thermoplastic compositions, but such compositions generally lack in adhesive grab so that virtually no adhesion to the body is obtained.

It is an object of the present invention to provide an absorbent article which is adhesively attached directly to the wearer's body.

It is an object of the present invention to provide an absorbent article which is adhesively attached directly to the wearer's body and which is small enough to be discrete and not noticeable through the wearer's outer garments.

It is an object of the present invention to provide an absorbent article which is adhesively attached directly to the wearer's body in the sensitive pudendal area.

It is another object of the present invention to provide a sanitary napkin which uses an adhesive having specific rheological properties to secure the sanitary napkin directly to the wearer in the sensitive pudendal area.

It is yet another object of the present invention to provide a sanitary napkin which is comfortable to wear and can be readily removed with little or no pain or discomfort to the wearer in the sensitive pudendal area.

It is yet another object of the present invention to provide a sanitary napkin with the desirable characteristics of a hydrogel adhesive, but without the drawbacks or disadvantages.

Other objects and advantages of the present invention will become apparent from the detailed description and accompanying drawings which follow.

SUMMARY OF THE INVENTION

The article of the present invention includes a sanitary napkin having an absorbent core with at least one body-facing surface designed to be positioned against the wearer's body and a pressure sensitive adhesive secured to the body-facing surface. In one aspect, the article is limited in dimension and includes a hot melt adhesive to be pressed against the wearer's pudendal region and characterized by a midblock Tg of less than −10° C., a G' (storage modulus) less than $15 \times 10^4$ dynes/cm$^2$ at 10 rad/s. (25° C.), a G" (loss modulus) of 1 to $6 \times 10^4$ dynes/cm$^2$, a tensile strength greater than 10 psi, and requiring no subsequent curing operation after cooling. In one aspect, the article includes an adhesive to be pressed against the wearer's pudendal region which has an adhesive weight less than 1500 mg per square inch and a tan delta residing inside a quadrangle ABCD wherein said quadrangle ABCD is defined by graphically plotting frequency in radians per second versus tan delta referenced to about 20° Centigrade of the adhesive, the quadrangle ABCD having as points A and D a tan delta of about 0.01 and about 0.6 respectively at a frequency of about 0.1 radians per second and points B and C at a tan delta of about 0.1 and about 1.7 respectively at a frequency of about 1000 radians per second.

DETAILED DESCRIPTION

The present invention provides a disposable absorbent article to be secured directly to the body of a wearer by a hot melt, pressure sensitive adhesive. The article of the present invention applies to a disposable absorbent article in the form of a catamenial device, i.e., a sanitary napkin. As used herein, the term "sanitary napkin" refers to an article which is worn by females adjacent to the pudendal region and which is intended to absorb and contain various exudates which are discharged from the body, such as, blood, menses, and urine. The sanitary napkin is intended to be discarded after a single use. Interlabial devices which reside partially within and partially external of the female wearer's vestibule are also within the scope of this invention.

The article of the present invention provides a hot melt pressure sensitive adhesive which adheres well to the human skin and hair in the sensitive pudendal area.

The article of the present invention provides a sanitary napkin incorporating a hot melt adhesive for bonding to sensitive areas of the human body which adhesive functions like a hydrogel but requires no subsequent cure.

Figure 1:
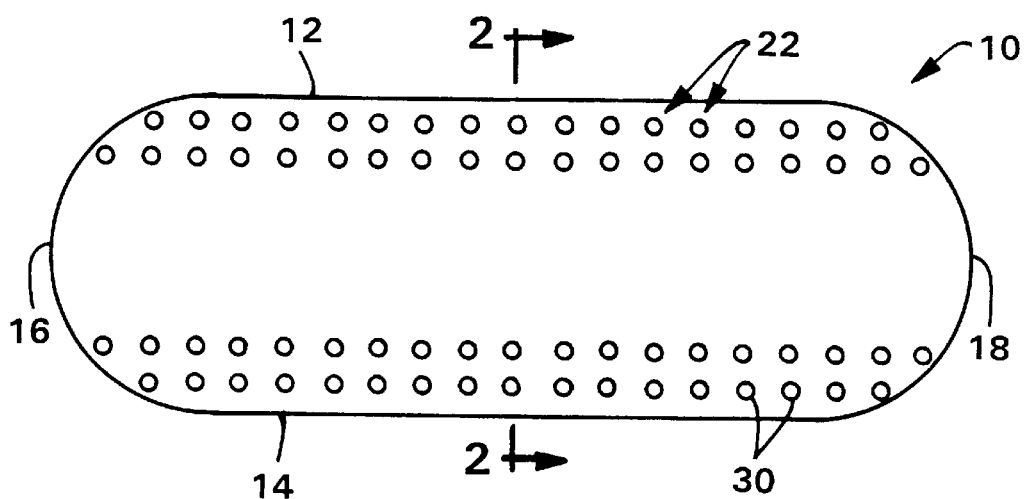
FIG. 1 is a top, plan view of an absorbent article showing one embodiment of the invention.
Figure 2:
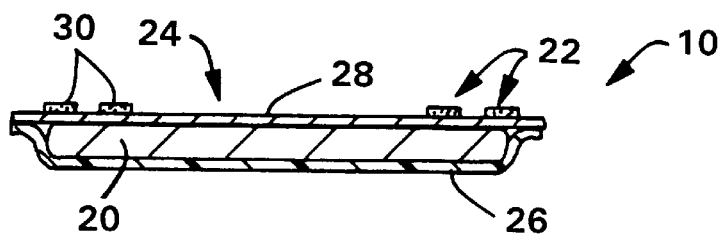
FIG. 2 is a cross-sectional view of FIG. 1 taken along line 2—2.

Referring now to FIG. 1 and FIG. 2, sanitary napkin 10 is depicted as having generally race track shape. Sanitary napkin 10 can have any variety of shapes, e.g., such as by way of example, hourglass, oval, and others. Sanitary napkin 10 has a pair of longitudinal sides 12 and 14, transverse ends 16 and 18, an absorbent core 20, and a body-side adhesive 22. Sanitary napkin 10 has at least one major surface 24 adapted to be positioned adjacent to a wearer's body. Surface 24 is soft and liquid-permeable. Fluid-impermeable baffle 26 is positioned distally from the body-facing surface 24.

Longitudinal sides 12 and 14 are between five (5) and nine (9) inches in length, preferably no longer than seven (7) inches. Transverse sides 16 and 18 are between two (2) and three and one-half (3.5) inches in length, preferably no longer than three (3) inches. The limitations on the sizes of the longitudinal and transverse sides are important so that the sanitary napkin of the present invention is not so large as to be uncomfortable to the wearer and is small enough to be discrete and not noticeable through the wearer's outer garments.

Absorbent core 20 may-be a material which is generally compressible, comfortable, non-irritating to the wearer's skin and capable of absorbing and containing body exudates such as urine, menses, blood, and the like. Absorbent core 20 maintains its integrity when wetted during use. The absorbent core 20 can be manufactured into different shapes and from a variety of liquid-absorbent materials commonly known in the disposable absorbent article art. For example, absorbent materials such as cellulose fibers, wood pulp, regenerated cellulose, or cotton fibers can be used. Such fibers may be chemically or physically modified. The absorbent core 20 may include any of the above fibers in combination with other materials, both natural and synthetic, such as hydrophilic foams, hydrophilic polymers, or the like. Wood pulp is frequently the material of choice primarily because it is inexpensive and readily available. The absorbent core 20 also may include a thin absorbent layer of material such as tissue, fabric, or the like made of cellulosic fibers. The absorbent core 20 also can include one or more superabsorbent materials. By "superabsorbent" is meant a hydrocolloid material capable of absorbing an amount of water which is at least ten times the weight of the hydrocolloid particles in the dry form and preferably from about 15 to 70 times the dry weight. Such materials are further described in U.S. Pat. No. 5,247,072 issued on Sep. 21, 1993 to Ning et al.

Baffle 26 is designed to permit the passage of air and moisture vapor to the outer surface while blocking the passage of liquids. The baffle 26 may be made from one or more polymeric films such as polyethylene, polypropylene, cellophane, or a film/non-woven laminate, or the like. The baffle 26 can also be constructed from a liquid-permeable material which has been treated or coated to become liquid impervious.

Referring now to FIG. 2, the sanitary napkin 10 includes a liquid-permeable cover 28 having a body-facing surface 24. The cover 28 is positioned adjacent to the absorbent core 20. The cover 28, which is designed to contact the wearer's body, can be made from various polymeric films which are provided with apertures for fluid migration into the absorbent core, or from woven or non-woven fibers or strands produced from natural or synthetic materials which are easily penetrated by body fluids. Thermoplastic polymer films made from polyethylene or polypropylene are preferred. Other acceptable covers are produced by laminating film and fiber substrates. It can be beneficial to provide apertures or to emboss (not shown) the cover 28 to increase the rate at which the body fluids can penetrate down and into the absorbent core 20.

The body-side adhesive 22 is positioned adjacent to the cover 28 in an open, substantially rectangular pattern of small discrete dots or adhesive members 30 so as to leave numerous areas free from adhesive. The adhesive members 30 can have a surface area of about 0.03 square centimeters ($cm^2$) to about 20 $cm^2$ and preferably about 0.15 $cm^2$ to about 15 $cm^2$.

As measured from the body-facing surface 24 of the cover 28, the adhesive members 30 can have a thickness of about 0.01 millimeters to about 2 millimeters.

The weights of adhesive are limited to less than about 1500 mg/$in^2$, preferably less than about 800 mg/$in^2$. The limitations on weight of adhesive are important to provide the correct adhesive characteristics for applying directly to the wearer's pudendal region.

The dot pattern of FIG. 1 contains approximately the least amount of body-side adhesive 22 required to obtain sufficient adherence to achieve the desired result and provide a satisfactory removal comfort. Generally, the adhesive 22 is secured to less than about 90 percent of the area of the body-facing surface 24, preferably less than about 70 percent of the area, and most preferably less than about 20 percent of the area.

A suitable adhesive pattern may be selected for applying the adhesive 22 to the body-facing surface 24 of the sanitary napkin 10, such that it is consistent with the concentration of adhesive 22 desired on the body-facing surface 24 yet allowing the sanitary napkin 10 to retain the requisite amount of absorbency. For example, adhesive patterns can be oval, swirls, various linear or non-linear arrays of adhesive longitudinally, and/or transversely oriented and reticulated webs having unobstructed interstices between the adhesive fibers or combinations thereof. The adhesive patterns may be open or closed. By "open" is meant that the adhesive can have an intermittent or continuous pattern which does not substantially cover one or more of the transverse ends 16 and/or 18 of the sanitary napkin 10. "Closed" means the adhesive would encircle the absorbent core 20. Preferably, the pattern of the adhesive 22 substantially corresponds to the configuration of the absorbent core 20.

Adhesive 22 is applied in a pattern which is symmetrical about an axis which bisects the sanitary napkin 10 and divides the sanitary napkin 10 into substantially equal portions. This symmetrical pattern provides the wearer a balanced feel when wearing the sanitary napkin 10. The symmetrical pattern also reduces the perception of any associated discomfort when the sanitary napkin 10 is removed from the body.

The adhesive 22 can be applied to the body-facing surface 24 by screen printing or extruding the adhesive 22 from one or more nozzles onto the body-facing surface 24 as described in the commonly assigned U.S. Pat. No. 4,995,333 issued to Keller et al. on Feb. 26, 1991.

The article of the present invention provides a hot melt adhesive for bonding to sensitive areas of the human body. The article of the present invention provides a hot melt pressure sensitive adhesive which adheres well to the human skin and hair and which can be removed without causing painful discomfort.

The article of the present invention includes a hot melt pressure sensitive adhesive which comprises at least one block copolymer and a liquid diluent, the adhesive being characterized by a midblock Tg of less than $-10°$ C., a G' (storage modulus) less than $15 \times 10^4$ dynes/cm$^2$ at 10 rad/s. ($25°$ C.), generally at least $1 \times 10^4$ and preferably 4 to $10 \times 10^4$ dynes/cm$^2$; a G" (loss modulus) of 1 to $6 \times 10^4$ dynes/cm$^2$ and a tensile strength greater than 10 psi exhibits superior properties, these properties being obtained without the need for any curing operation after cooling.

In one aspect, the article of the present invention includes a hot melt pressure sensitive adhesive comprising 1 to 20 parts of a high molecular weight rubber triblock or radial block copolymer, 0 to 20 parts high molecular weight diblock rubber, 0 to 10 parts by weight of other compatible high molecular weight polymers; 0 to 30 parts by weight end block resin; 60 to 95 parts by weight oil or other liquid midblock diluent; 0 to 50 parts by weight of a solid tackifier which is compatible with the polymer midblock, and 0 to 3 parts by weight anti-oxidant; the parts to total 100 parts by weight.

As used herein, the term "high molecular weight rubbers" are those with a viscosity at $25°$ C. of above 1,000 centipoise in toluene at a concentration of 20% by weight.

In the case of the high viscosity triblock copolymers employed herein, they may have the more general configuration A-B-A wherein the polymer blocks A are non-elastomeric polymer blocks which, as homopolymers, have glass transition temperatures above $20°$ C., while the elastomeric polymer blocks B are isoprene, or butadiene which may be partially or substantially hydrogenated or mixtures thereof. Further, the copolymers may be linear or branched. Typical branched structures contain an elastomeric portion with at least three branches which can radiate out from a central hub or can be otherwise coupled together. The non-elastomeric blocks may comprise homopolymers or copolymers of vinyl monomers such as vinyl arenes, vinyl pyridines, vinyl halides, and vinyl carboxylates, as well as acrylic monomers such as acrylonitrile, methacrylonitrile, and esters of acrylic acids. Monovinyl aromatic hydrocarbons include particularly those of the benzene series such as styrene, vinyl toluene, vinyl xylene, ethyl vinyl benzene as well as dicyclic monovinyl compounds such as vinyl naphthalene and the like. Other non-elastomeric polymer blocks may be derived from alpha olefins, alkylene oxides, acetals, or urethanes. Styrene is preferred.

The elastomeric block component making up the remainder of the copolymer is isoprene or butadiene which may be hydrogenated as taught, for example, in U.S. Pat. No. 3,700,633. This hydrogenation of butadiene may be either partially or substantially complete. Selected conditions may be employed for example to hydrogenate the elastomeric butadiene block while not so modifying the vinyl arene polymer blocks. Other conditions may be chosen to hydrogenate substantially uniformly along the polymer chain, both the elastomeric and non-elastomeric blocks thereof being hydrogenated to practically the same extent, which may be either partial or substantially complete. Hydrogenated polymers are preferred to minimize degradation during processing, which is a more severe problem with higher molecular weight polymers.

The high viscosity triblock copolymer of the invention can have a broad range of non-elastomeric end block to elastomeric center block ratio of approximately about 5:95 or less to about 40:60 or higher. Examples of high viscosity triblock copolymers which can be utilized to achieve one or more of the novel properties of the present invention are styrene-ethylene-butylene-styrene block copolymers (SEBS) available from Shell Chemical Company and Pecten Chemical Company (divisions of Shell Oil Company) under trade designations Kraton G 1651, Kraton G 1654, Kraton G 4600, Kraton G 4609 and the like. Other grades of (SEBS) polymers can also be utilized in the present invention provided such SEBS polymers exhibit the required high viscosity. Such SEBS polymers include high viscosity Kraton G 1855X which has a Specific Gravity of 0.92, Brookfield Viscosity of a 25 weight percent solids solution in toluene at $25°$ C. of about 40,000 cps or about 8,000 to about 20,000 cps at a 20 weight percent solids solution in toluene at $25°$ C. Although the typical ratio values for Kraton G 1651, 4600, and 4609 are approximately about 33:67 and for Kraton G 1855X approximately about 27:73, as noted previously, these ratios can vary broadly from the typical product specification values.

It is preferred that the adhesive additionally contain 1 to 20, preferably 3 to 8, parts by weight of a high molecular weight (i.e., viscosity >1000 cps at $25°$ C. at 20% in toluene) diblock polymer of the general A-B configuration where A and B are as described previously. Preferred are Kraton G 1701X or 1702X which are both styrene ethylene propylene diblock polymers. Kraton G1702X is most preferred.

While it is preferred the formulation contain some diblock polymer, the diblock may be replaced entirely or in part with another high molecular weight polymer which is compatible with the system. For example, polyisobutylene (e.g., Vistanex from Exxon), polyisoprene (e.g., from Kuraray), or styrene/butadiene copolymer (e.g., Plioflex from Goodyear) may be used in amounts of about 2 to 10 parts by weight.

As will be described herein below, various additives are known to associate with the particular blocks (domains) of the block polymer(s), altering the behavior of those portions accordingly. In more detail, the mid-block portion or domain (i.e., the "B-block") of the polymer generally has a very low Tg (e g., on the order of about −50° C.). As other mid-block compatible components such as plasticizing oils and tackifiers are added, these components associate with the B domains swelling them and generally resulting in a change in the Tg thereof. For most pressure sensitive adhesive applications, a Tg in the range of about 0° C. to 25° C., preferably about 15° C., is desirable. However, for use herein mid-block Tg ranges of less than about −10° C. are required.

Thus, there is also present in the adhesive about 60 to 95 parts by weight, preferably 70 to 80 parts, of an oil or other liquid diluent which is primarily aliphatic in character and is compatible with the polymer midblock. Included in these materials are plasticizers such as paraffinic and naphthenic petroleum oils, highly refined aromatic-free paraffinic and naphthenic food and technical grade white petroleum mineral oils, and liquid tackifiers such as the synthetic liquid oligomers of polybutene, polypropene, and polyterpene. The synthetic series process oils are high viscosity oligomers which are permanently fluid liquid monolefins, isoparaffins, or paraffins of moderate to high molecular weight. Liquid plasticizing or tackifying diluents include polyterpenes such as Wingtack 10 available from Goodyear, and Escorez 2520 based on a C5 feed stream available from Exxon Chemical. Other liquid diluents would include polyisoprene, available as LIR 50 from Kuraray, Amoco's polybutenes available under the name Indopol. Most preferred are paraffinic oils in combination with Escorez 2520, a polymerized C5 petroleum feed stream.

There may also be present up to 50 parts, preferably 10 to 20 parts by weight of a solid tackifier (i.e., one having a Ring and Ball softening point above 25° C.) which is compatible with the midblock. Suitable tackifiers include any compatible resins or mixtures thereof such as (1) natural or modified rosins such, for example, as gum rosin, wood rosin, tall-oil rosin, distilled rosin, hydrogenated rosin, dimerized rosin and polymerized rosin; (2) glycerol and pentaerythritol esters of natural or modified rosins, such, for example as the glycerol ester of pale, wood rosin, the glycerol ester of hydrogenated rosin, the glycerol ester of polymerized rosin, the pentaerythritol ester of hydrogenated rosin, and the phenolic-modified pentaerythritol ester of rosin; (3) copolymers and terpolymers of natural terpenes, e.g., styrene/terpene and alpha methyl styrene/terpene; (4) polyterpene resins having a softening point, as determined by ASTM method E28,58T, of from about 80° to 150° C.; the latter polyterpene resins generally resulting from the polymerization of terpene hydrocarbons, such as the bicyclic monoterpene known as pinene, in the presence of Friedel-Crafts catalysts at moderately low temperatures; also included are the hydrogenated polyterpene resins; (5) phenolic modified terpene resins and hydrogenated derivatives thereof, for example, as the resin product resulting from the condensation, in an acidic medium, of a bicyclic terpene and phenol; (6) aliphatic petroleum hydrocarbon resins having a Ball and Ring softening point of from about 70° to 135° C.; the latter resins resulting from the polymerization of monomers consisting of primarily of olefins and diolefins; also included are the hydrogenated aliphatic petroleum hydrocarbon resins; (7) alicyclic petroleum hydrocarbon resins and the hydrogenated derivatives thereof; and (8) aliphatic/aromatic or cycloaliphatic/aromatic copolymers and their hydrogenated derivatives.

Preferred tackifiers for use herein include polyterenes such as Wingtack 95 from Goodyear; aliphatic resins such as Hercures C from Hercules; cycloaliphatic resins such as Eastotac H100 from Eastman; and aliphatic/aromatic or cycloaliphatic/aromatic resins such as ECR 149B or ECR 179A from Exxon Chemical. Most preferred are the aliphatic or cycloaliphatic resins while the least desirable are the rosin esters or phenolic modified polyterpenes.

The desirability and selection of the particular tackfying agent is, in large part, dependent upon the specific block copolymer employed.

Additionally, the adhesive may incorporate up to 30 parts by weight of an end block resin. End block resins are those resins which reside predominantly in the non-elastomer domains of the rubber after the adhesive is cooled. Representative of such resins are the primarily aromatic resins based on mixed C9 petroleum distillation streams such as the Hercures materials available from Hercules, or resins based on pure or mixed monomer streams of aromatic monomers such as homo or copolymers of vinyl toluene, styrene, alpha-methyl styrene, coumarone or indene. Preferred are those based on alpha-methyl styrene available from Hercules under the Kristalex trade name. If present, the end block resin is generally used in an amount of 5 to 30 parts by weight, preferably less than 20 parts.

Optionally there may also be present 0 to 5% by weight of a wax component such as the polyethylene waxes available from Allied-Signal under the A-C symbol. If used, the wax is generally present in an amount of at least 2 parts by weight.

Finally, antioxidants typically used in the production of rubber based pressure sensitive adhesives may be present in an amount up to about 3 parts by weight. Among the applicable stabilizers or antioxidants utilized herein are included high molecular weight hindered phenols and multi-functional phenols such as sulfur and phosphorous-containing phenols. Hindered phenols may be characterized as phenolic compounds which also contain sterically bulky radicals in close proximity to the phenolic hydroxyl group hereof. In particular, tertiary butyl groups generally are substituted onto the benzene ring in at least one of the ortho positions relative to the phenolic hydroxy group. The presence of these sterically bulky substituted radicals in the vicinity of the hydroxyl group serves to retard its stretching frequency and, correspondingly, its reactivity. This steric hindrance thus provides the phenolic compound with its stabilizing properties. Representative hindered phenols include: 1,3,5-trimethyl 2,4,6-tris (3,5-di-tert-butyl-4-hydroxybenzyl) benzene; pentaerythrityl tetrakis-3(3,5-ditert-butyl-=hydroxyphenyl)-propionate; 4,4'-methylenebis (2,6-tertbutylphenol); 4,4'-Thiobis (6-tert-butyl-o-cresol); 2,6-di-tertbutylphenol; 6-(4-hydroxyphenoxy)-2,4-bis(n-octylthio)-1,2,5-triazine; di-n-octadecyl3,5-di-tert-butyl4-hydroxybenzyl phosphonate; 2-(n-octylthio)ethyl 3,5-ditert-butyl4-hydroxybenzoate; and sorbitol hexa[3-(3,5-ditert-butyl4-hydroxyphenyl)-propionate].

The triblock rubber provides the set of the adhesive into a gelatinous solid, while the diblock rubber improves the tack of the formulation, as does the liquid resin. The substitution of liquid resin for oil also inhibits bleed into the release paper against which the adhesive is stored. The end block resin also provides strength to the adhesive formulation while lowering its melt viscosity by reducing the self-association of the rubber end blocks when molten. In formulating the adhesives, predominately liquid diluents are used to ensure a low Tg for the matrix (midblock portion) of the formulation. A low Tg leads to fast polymer relaxation times which in turn lead to low pain upon removal of the adhesive.

The adhesive may be prepared from about 10 parts of polymer, equally split between triblock and diblock, preferably Kraton G 1651 and Kraton G1702, respectively. These rubbers are used in combination with 5 to 30 parts, preferably 10–20 parts, of end block resin, with Kristalex α-methyl styrene resins most preferred. The remainder of the product is diluent and tackifier. The lower the blend Tg of the remainder, the less tack and lower-peel the adhesive will exhibit. Preferably the remainder is liquid diluent, either oil or a blend of oil and liquid tackifier. Most preferred is about a 50/50 blend of a paraffin oil (such as Kaydol available from Witco) and liquid tackifier. The most preferred liquid tackifier is Escorez 2520, a polymerized C, petroleum feed stream which has a Tg of −16° C. A particularly preferred hot melt adhesive composition comprises 3 to 8 parts of the triblock polymer, 3 to 8 parts diblock, 5 to 30 parts end block resin, the remainder (to 100 parts) comprising a liquid diluent, a liquid tackifier and optionally a solid tackifier such that the blend of the diluent and tackifier(s) exhibits a Ring and Ball softening point below 25° C.

A Rheometrics Dynamic Mechanical Analyzer (Model RDA 700 or RDSII) may be used to obtain the elastic (G') and loss (G") moduli versus temperature. The instrument can be controlled by Rhios software version 4.3.2. The shear storage or elastic modulus (G') and the shear loss modulus (G") are calculated by the software from torque and strain data. Their ratio, G"/G', also known as the tan delta, then is calculated.

The novel adhesive in accordance with the article of the present invention is a pressure sensitive hot melt adhesive, characterized as having specific rheological properties. Rheological analysis determines viscoelastic properties of the polymers. Further explanations of polymer rheology and measurement may be found in *Viscoelastic Properties of Polymers*, John D. Ferry, John Wiley & Sons, third edition, pages 264–280 (1980); "Studies of Triblock Copolymer-Tackifying Resin Interactions by Viscoelasticity and Adhesive Performance," Mun Fu Tse, *Journal of Adhesion Science Technology*, Vol. 3 No. 7, pages 551–570 (1989); and test procedure ASTM-D 4440-84 the disclosures of which are incorporated herein by reference and made a part hereof.

It is critical to the article of the present invention that the adhesive have a rheology property, tan delta (referenced to 20° Centigrade), ranging from about 0.01 to about 0.6 and preferably from about 0.06 to about 0.48 and most preferably from about 0.06 to about 0.40 at a frequency of about 0.1 radians per second and a tan delta ranging from about 0.1 to about 1.7, preferably from about 0.20 to about 1.5 and most preferably from about 0.6 to about 1.5 at a frequency of about 1000 radians per second.

Figure 3:
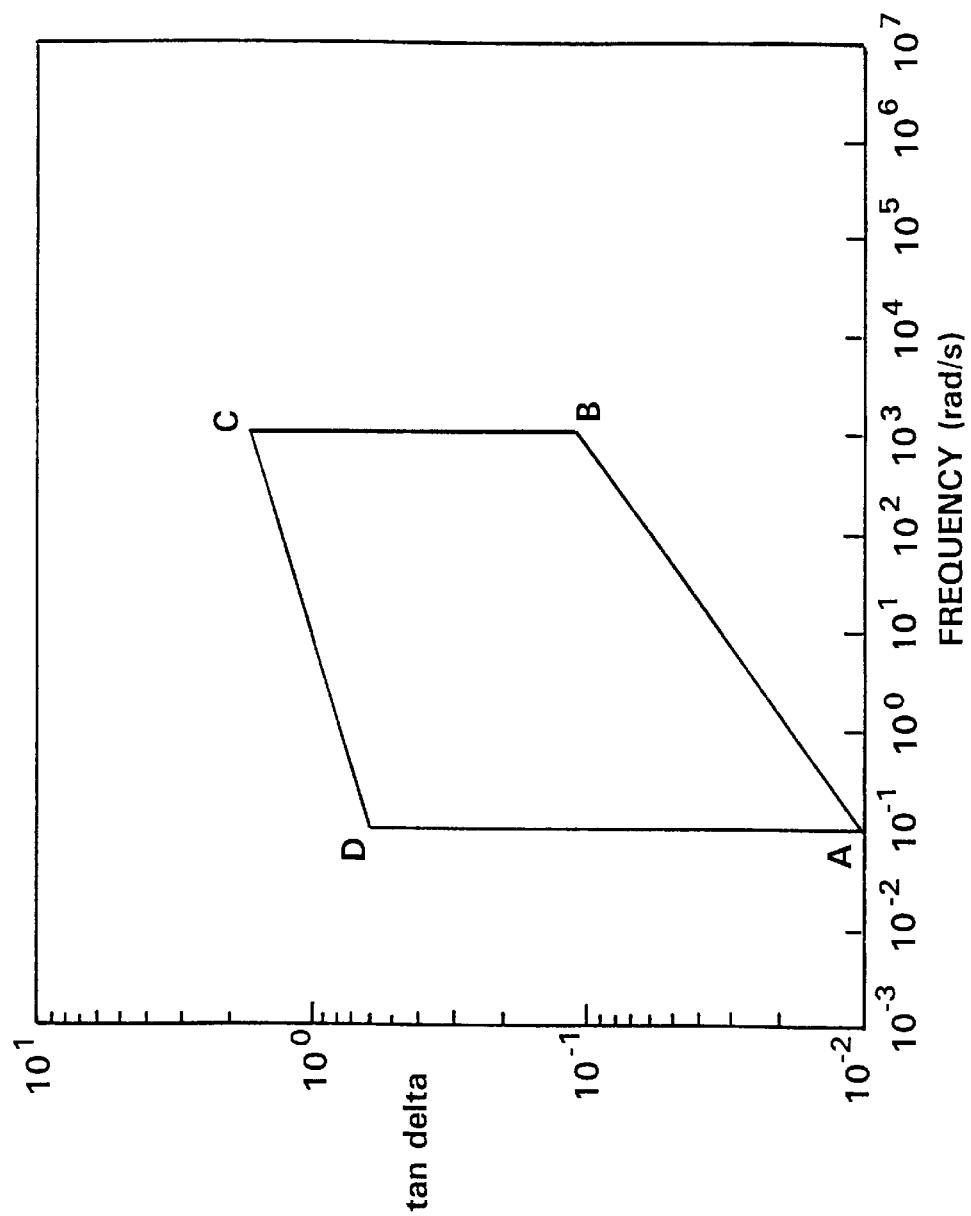
FIG. 3 is a graphical plot of frequency (in radians per second) versus the rheological property tan delta illustrating the quadrangle ABCD.

The novel adhesive in accordance with the article of the present invention has a tan delta, (referenced to 20° Centigrade), inside the Quadrangle ABCD between the frequency range of about 0.1 radians per second to about 1000 radians per second, as seen in FIG. 3. The sides defining the Quadrangle ABCD are determined by plotting as points A, D, B and C the crucial range of tan delta described above at the lower and upper frequencies, i.e., 0.1 radians/second and 1000 radians/second, respectively. Generally, adhesives having a tan delta outside of the Quadrangle ABCD provide insufficient adhesion to support the sanitary napkin 10 to the wearer or not allowing the sanitary napkin 10 to be comfortably removed. For example, referring to FIG. 3, adhesives having tan delta values below line AB at frequencies of about 0.1 to about 100 radians per second lack sufficient flow and wet-out characteristics to provide initial adhesion or quick-stick of the sanitary napkin 10 to the body. Adhesives having a tan delta below line AB at frequencies of about 150 to about 1000 radians per second lack sufficient adhesion to keep the sanitary napkin 10 securely and comfortably attached to the body of the wearer during use.

Adhesives having tan delta values greater than line CD, at frequencies of about 0.1 radians per second to about 100 radians per second lack sufficient cohesive strength to remain in place on the sanitary napkin 10 during storage, use and removal. While adhesives having a tan delta greater than line CD at frequencies of about 150 to about 1000 radians per second cause discomfort during removal of the soiled sanitary napkin 10.

The novel adhesive in accordance with the article of the present invention has a Secondary Transition Frequency peak within the Quadrangle ABCD and a Primary Transition Frequency peak at a frequency greater than about 1000 radians per second. The "Primary Transition Frequency" and "Secondary Transition Frequency" peaks are determined by amplitude. The peak having the greater amplitude is the primary peak regardless of its occurrence in the frequency sweep. The peaks are determined by graphically plotting, on a log/log scale, the frequency (in radians per second) versus tan delta (referenced to 20° C.) of the adhesive 22 using a time-temperature superposition master curve between the frequencies of about 0.001 and $10^7$ radians per second. These curves are determined using a Rheometrics Dynamic Spectrometer (RDS II E), which can be obtained from Rheometrics, Inc. located at 1 Possum Town Road, Piscataway, N.J. 08854. The rheological quantities for tan delta are measured on bulk adhesive samples not suspended on any substrate and having a thickness of approximately 2 to 3 millimeters. The adhesive was cut into a 25 millimeter diameter circle and placed between two 25 millimeter parallel plate fixtures of the Rheometrics Dynamic Spectrometer. The upper platen was lowered onto the sample until the normal force meter indicates a slight deflection. The samples are allowed to equilibrate at a selected test temperature before analyzing. A minicomputer governs the application of a 1% peak-to-peak shear strain to the sample. The frequency of the application can be controlled to a fraction of a radian/sec. The values of the loss tangent (tan delta) are calculated from geometry factors, peak-to-peak amplitude of the torque signal, and phase lag of the torque output wave. Typically, a computer using Rhios software available from Rheometrics, Inc. is used to control the operation of the apparatus and to calculate values for time-temperature superposition using known techniques.

Frequency sweeps from 0.1 rad/s to 100 rad/s are run at 100 increments from −60° C. to 120° C. The Rhios software shifts the curves relative to a reference temperature of 20° C. From these shifted curves, a "master" curve can be generated.

The article of the present invention incorporates an adhesive having a peel force ranging from about 50 grams to about 750 grams at a peel rate of about 50 millimeters per minute to about 3500 millimeters per minute.

Peel strength data were obtained by preparing adhesive test laminates as follows. The adhesive was coated onto a substrate such as a silicone coated release paper. The adhesive pattern used for conducting the tests was two (2) lines of adhesive each approximately 6 mm wide running parallel to the longitudinal axis of the substrate. The adhesive lines were spaced about 38 millimeters apart and equidistant from the center of the laminate. The adhesive was slot coated onto a substrate using techniques known in the art. The adhesive/substrate was then contacted with a nonwoven material, spunbond polypropylene. The spunbond had a basis weight of 0.6 ounces per square yard. The substrate/spunbond laminate was subjected to a pressure ranging from about 35 pounds per square inch gauge (psig) to about 80 psig from a heated nip roller to ensure adequate transfer of the adhesive onto the spunbond material. The nip temperature ranged from about 25° Centigrade to about 150° Centigrade. Total adhesive add on to the spunbond was approximately 263 grams per square meter. Surface area covered by the adhesive was approximately 16–25 percent. The substrate was then removed and the adhesive laminates were then tested for peel strength.

The peel strength of the adhesive was determined using a modified Pressure Sensitive Tape Council 180° peel resistance test (PSTC-1) described below. PSTC-1 is a standardized test procedure that is described in greater detail on page 23 of the tenth edition of *Test Methods* copyright 1992, available from Pressure Sensitive Tape Council 401 North Michigan Ave., Chicago, Ill. 60611-4267 the disclosure of which is incorporated herein and made a part hereof. The peel adhesion values were determined according to the following procedure.

A double sided adhesive tape of approximately 13 millimeters wide was secured to the top and bottom edges of a stainless steel test plate having dimensions of about 100 millimeters wide and 152 millimeters long. The adhesive tape was 3M #665 available from the 3M Corporation located in St. Paul, Minn. A polyethylene film 0.05 millimeters thick, male embossed, was secured to the double sided tape with male embossed side as the test surface. The polyethylene film is available from Edison Plastic, located in Washington, Ga. One end of the spunbond, i.e. the end that will be the leading end, was rigidly secured to a leading strip of non-stretchable material. The leading strip should be stronger than the peel strength of the adhesive. The test sample was pressed down on the polyethylene film with a 2043 gram mechanical roller, (available from Chemsultant International, Mentor, Ohio). The 180° peel was then immediately conducted on a Materials Test System model 810 available from MTS Corp., Minneapolis, Minn. 55424. When placing the test specimen in the tester, the jaws of the tester were initially set 17.78 cm apart. The steel test panel was secured in the stationary jaw (1.27 cm) with the unsecured leading strip extending past the position of the stationary jaw. The leading strip was then doubled back and clamped in a centered arrangement within the moving jaw of the tester. The tester was activated to conduct the 180° peel test. The moving jaw travelled a total distance of 20.32 cm, with the adhesive tested in the middle 10.16 cm. The MTS can be programed to control the peel rate using a microprofiler model 458.91.

While the invention has been described in conjunction with a specific embodiment, it is to be understood that many alternatives, modifications, and variations will be apparent to those skilled in the art in light of the foregoing description. Accordingly, this invention is intended to embrace all such alternatives, modifications, and variations which fall within the spirit and scope of the appended claims.

What is claimed is:

1. A catamenial device having a body-side adhesive, comprising:

a) a cover having a body-facing surface and a garment-facing surface;

b) an absorbent core adjacent to said garment-facing surface; and c) a pressure sensitive adhesive secured to said body-facing surface, wherein said adhesive referenced to about 20° C., has a rheological property tan delta ranging from about 0.01 to about 0.6 at a frequency of about 0.1 radians per second and a tan delta ranging from about 0.1 to about 1.7 at a frequency of about 1000 radians per second.

2. The catamenial device having a body-side adhesive of claim 1 wherein said adhesive is a hot melt adhesive and said body-facing surface is limited in dimension to the wearer's pudendal region.

3. The catamenial device having a body-side adhesive of claim 2 wherein said adhesive is secured to less than about 90 percent of the body-facing surface area.

4. The catamenial device having a body-side adhesive of claim 3 wherein said adhesive includes an array of independent adhesive members, said members each having a surface area between about 0.03 cm$^2$ to about 20 cm$^2$ and a thickness of about 0.01 millimeters to about 2 millimeters.

5. The catamenial device having a body-side adhesive of claim 4 wherein said adhesive has a peel force ranging from about 50 grams to about 750 grams at a peel rate of about 50 millimeters per minute to about 3500 millimeters per minute.

6. The catamenial device having a body-side adhesive of claim 5 wherein said tan delta has a primary Transition Frequency peak at a frequency greater than about 1000 radians per second.

7. The catamenial device having a body-side adhesive of claim 6 wherein said tan delta has a secondary Transition Frequency peak between a frequency range of about 0.1 and about 1000 radians per second.

* * * * *